US011964137B2

(12) United States Patent
Mirigian et al.

(10) Patent No.: US 11,964,137 B2

(45) Date of Patent: Apr. 23, 2024

(54) CRYOTHERAPEUTIC DELIVERY DEVICE

(71) Applicant: Boston Scientific Scimed Inc., Maple Grove, MN (US)

(72) Inventors: Mark David Mirigian, Clonmel (IE); Robert Hannon, Clonmel (IE); James Michael English, Cahir (IE); Aine McConville, Clonmel (IE); Aideen Bridget Beatty, Galway (IE); Martin L. Fawdry, Galway (IE); Peter M. McKenna, Crumlin (IE); Sophie A. Gannon, Galway (IE); Sara J. Callagy, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 885 days.

(21) Appl. No.: 16/740,927

(22) Filed: Jan. 13, 2020

(65) Prior Publication Data

US 2020/0222632 A1 Jul. 16, 2020

Related U.S. Application Data

(60) Provisional application No. 62/793,296, filed on Jan. 16, 2019.

(51) Int. Cl.

| | |
|---|---|
| ***A61M 5/31*** | (2006.01) |
| ***A61J 1/14*** | (2023.01) |
| ***A61J 1/20*** | (2006.01) |
| ***A61M 1/02*** | (2006.01) |
| ***A61M 5/24*** | (2006.01) |

(52) U.S. Cl.

CPC .......... *A61M 5/3145* (2013.01); *A61J 1/1443* (2013.01); *A61J 1/2075* (2015.05);

(Continued)

(58) Field of Classification Search

CPC .............. A61M 5/3145; A61M 1/0281; A61M 5/2422; A61M 1/0218; A61M 2005/2411;

(Continued)

(56) References Cited

U.S. PATENT DOCUMENTS

| | | | | |
|---|---|---|---|---|
| 3,977,401 A * | 8/1976 | Pike | A61M 5/2053 604/144 |
| 5,335,824 A * | 8/1994 | Weinstein | B05B 11/0038 222/82 |

(Continued)

FOREIGN PATENT DOCUMENTS

| | | | | |
|---|---|---|---|---|
| DE | 19532015 A1 * | 3/1997 | B01F 11/0082 |
| WO | WO-2014080430 A1 * | 5/2014 | A61J 1/16 |
| WO | 2019/018272 A1 | 1/2019 | |

OTHER PUBLICATIONS

International Search Report and Written Opinion received for PCT Patent Application No. PCT/US2020/013313, dated May 8, 2020, 19 pages.

*Primary Examiner* — Susan S Su
*Assistant Examiner* — Ted Yang
(74) *Attorney, Agent, or Firm* — Seager, Tufte & Wickhem, LLP

(57) ABSTRACT

A device for aseptic delivery of biological material from a vial includes a tubular barrel, a filter assembly, and a dispersion assembly. The dispersion assembly is at least partially disposed within the tubular barrel. The dispersion assembly includes a dispersion element, a piston, and a one-way valve. The dispersion element is in fluid communication with the vial to disperse the biological material from the vial. The piston is disposed at the distal end of the dispersion assembly and is in sealing contact with the tubular barrel. The one-way valve forms a fluid passageway in fluid communication with the dispersion element and the tubular barrel. The one-way valve is configured to allow a (Continued)

flow of the dispersed biological material from the dispersion element, through the fluid passageway, and into the tubular barrel, and to prevent a flow of the dispersed biological material from the tubular barrel into the dispersion assembly.

19 Claims, 8 Drawing Sheets

(52) U.S. Cl.
CPC ........... *A61J 1/2086* (2015.05); *A61J 1/2096* (2013.01); *A61M 1/0281* (2013.01); *A61M 5/2422* (2013.01); *A61J 1/2082* (2015.05); *A61M 1/0218* (2014.02); *A61M 2005/2411* (2013.01); *A61M 2005/3123* (2013.01); *A61M 2005/3128* (2013.01); *A61M 2207/10* (2013.01)

(58) Field of Classification Search
CPC .. A61M 2005/3123; A61M 2005/3128; A61M 2207/10; A61M 2202/0437; A61J 1/1443; A61J 1/2075; A61J 1/2086; A61J 1/2096; A61J 1/2082
See application file for complete search history.

(56) References Cited

U.S. PATENT DOCUMENTS 5,441,539 A * 8/1995 Alchas .................... A61F 2/062 600/36
5,443,182 A * 8/1995 Tanaka ................ B01F 35/7164 222/137
5,779,668 A * 7/1998 Grabenkort ......... A61M 5/3129 604/218
5,902,745 A * 5/1999 Butler ..................... A61F 2/022 435/297.1
8,157,774 B1 * 4/2012 Altobelli ............. A61M 1/0281 604/319
9,814,843 B2 * 11/2017 Diaz ................... A61M 5/3202
11,464,704 B2 * 10/2022 Beatty ................... A61J 1/1443
2003/0069543 A1 * 4/2003 Carpenter ......... A61M 25/0084 604/190
2007/0060904 A1 * 3/2007 Vedrine ................. A61J 1/2096 604/411
2008/0091147 A1 * 4/2008 Lee ................... A61M 5/14566 604/190
2008/0294096 A1 * 11/2008 Uber, III ............. A61M 31/005 604/66
2009/0043282 A1 * 2/2009 Hughes ................. B01F 31/441 604/82
2010/0185156 A1 * 7/2010 Kanner ................... A61P 43/00 604/190
2017/0368226 A1 * 12/2017 Pilkington ........ A61M 5/31513
2018/0318572 A1 * 11/2018 Kraus ................... A61M 5/162
2019/0015298 A1 * 1/2019 Beatty ................... A61J 1/2096
2019/0321837 A1 * 10/2019 Bhogal ................... A61P 17/02
2019/0328977 A1 * 10/2019 Kirn .................... A61M 5/1782
2020/0330698 A1 * 10/2020 Ra ....................... A61M 5/3202
2023/0248899 A1 * 8/2023 Balasubramanian ........................ A61M 5/1582 604/500

* cited by examiner

CRYOTHERAPEUTIC DELIVERY DEVICE

CROSS REFERENCE TO RELATED APPLICATION

This application claims priority to Provisional Application No. 62/793,296, filed Jan. 16, 2019, which is herein incorporated by reference in its entirety.

TECHNICAL FIELD

The present invention relates to systems, devices, and methods for the storage and delivery of biological material to a patient. More specifically, the invention relates to systems, devices, and methods for the storage and delivery of cryotherapeutic biological material to a patient.

BACKGROUND

Biological materials for cellular therapy, such as allogenic or autologous transplant cells, are typically produced by aspirating stem cells from a donor or patient, respectively, and then isolating and differentiating the stem cells. The differentiated stem cells are then expanded to produce a quantity of the differentiated stem cells sufficient for the cellular therapy. Prior to storage, the differentiated stem cells are washed and suspended in a solution including proteins and a cryoprotectant, such as dimethyl sulfoxide (DMSO). The suspended cells are then transferred to bags or vials and frozen with liquid nitrogen at a slow, controlled rate.

The frozen suspended cells are transferred to a clinic and remain frozen until ready for use. The cells are thawed in the bags, and then transferred from the bags to specialized equipment for washing. The washing removes the cryoprotectant which can increase some side effects of the cellular therapy if not removed. In some cases, the equipment must be operated by specially trained professionals using specialized reagents. The use of the specialized equipment, professionals, and reagents is costly. In other cases, the equipment can use inexpensive saline solution instead of the specialized reagents, but requires centrifugation of the cells. The centrifugation can damage the cells and cause them to clump together, reducing the viability of the cells and the effectiveness of the cell therapy.

Once the transplant cells are washed of the cryoprotectant, they are transferred from the specialized equipment to a syringe or catheter for delivery to the patient. Each of the transfer steps, such as from bag to washing equipment and from the washing equipment to a syringe, exposes the cells to the atmosphere and introduces an increased risk of contamination and infection, especially in high-risk, immune-compromised patients. Thus, a device is needed to allow aseptic delivery of biological material from a vial and provide reliable usability.

SUMMARY

Example 1 is a device for aseptic delivery of biological material from a vial. The device includes a tubular barrel, a filter assembly, and a dispersion assembly. The tubular barrel includes a receiving end to accept a portion of the vial within the tubular barrel and a dispensing end opposite the receiving end. The filter assembly is fluidly connected to the dispensing end of the tubular barrel. The dispersion assembly has a proximal end configured to couple to the vial and a distal end opposite the proximal end. The dispersion assembly is configured to be at least partially disposed within the tubular barrel. The dispersion assembly includes a dispersion element, a piston, and a one-way valve. The dispersion element is configured to be in fluid communication with the vial to disperse the biological material from the vial. The piston is disposed at the distal end of the dispersion assembly. The piston is in sealing contact with the tubular barrel. The one-way valve forms a fluid passageway in fluid communication with the dispersion element and the tubular barrel. The one-way valve is configured to allow a flow of the dispersed biological material from the dispersion element, through the fluid passageway, and into the tubular barrel, and to prevent a flow of the dispersed biological material from the tubular barrel into the dispersion assembly.

Example 2 is the device of Example 1, wherein the filter assembly includes a filter medium, the filter assembly selectable between an open state wherein the filter medium prevents the biological material from passing through the filter assembly but permits liquid to pass through the filter assembly, a bypass state wherein the biological material can pass through the filter assembly to deliver the biological material, and, optionally, a closed state wherein no liquid or biological material can pass through the filter assembly.

Example 3 is the device of Example 2, wherein the filter assembly further includes a filter medium assembly configured to support the filter medium.

Example 4 is the device of Example 3, wherein the filter medium assembly is detachable from the filter assembly.

Example 5 is the device of any of Examples 2-4, wherein the filter assembly further includes a filter output port in fluid communication with the dispensing end of the tubular barrel when the filter assembly is in the open state, and a bypass output port in fluid communication with the dispensing end of the tubular barrel when the filter assembly is in the bypass state.

Example 6 is the device of Example 5, wherein the filter assembly further includes a filter base and a filter selector. The filter base includes a first section in fluid communication with the filter output port, a second section in fluid communication with the bypass output port, and a third section that is not in fluid communication with either of the filter output port or the bypass output port. The filter selector is rotatably coupled to the filter base. The filter selector includes a filter inlet in fluid communication with the tubular barrel. The filter selector is configured to fluidly connect the filter inlet to the first section, the second section, or the third section of the filter base as the filter selector rotates relative to the filter base.

Example 7 is the device of Example 6, wherein the filter assembly further includes a compression clasp coupled to the filter base to force the filter selector into sealing contact with the filter base and a wrench coupled to the filter selector.

Example 8 is the device of any of Examples 1-7, wherein the dispersion element comprises a wall forming a plurality of openings through the wall, the plurality of openings through the wall are sized to permit the passage of dispersed biological material through the wall and to prevent the passage of undispersed biological material through the wall.

Example 9 is the device of Examples 1-8, wherein the tubular barrel further includes a barrel ventilation passageway extending through a wall of the tubular barrel from a first location between the dispensing end and the receiving end to a second location adjacent to the receiving end.

Example 10 is the device of Example 9, wherein the tubular barrel further includes a one-way barrel vent valve within the barrel ventilation passageway and configured to allow the passage of gases away from the first location, prevent the passage of gases toward the first location, and prevent the passage of liquids.

Example 11 is a system for aseptic storage and delivery of biological material. The system includes a vial and the device according to any of Examples 1-10. The vial includes a tubular body to contain the biological material until delivery, a vial input port, and a vial output port including a luer activated valve. The proximal end of the dispersion assembly is configured to open the luer activated valve when coupled to the vial output port to bring the dispersion element into fluid communication with the vial.

Example 12 is the system of Example 11, wherein the vial further includes a vial ventilation passageway extending through a wall of the vial from vial output port to the vial input port.

Example 13 is the system of Example 12, wherein the vial further includes a one-way vial vent valve within the vial ventilation passageway and configured to allow the passage of gases away from the vial output port, prevent the passage of gases toward the vial output port, and prevent the passage of liquids.

Example 14 is a method for the aseptic delivery of biological material that is in an aseptically frozen and condensed state within a vial using a delivery device. The method includes thawing the biological material contained within the vial, coupling a vial output port of the vial to a proximal end of a dispersion assembly of the delivery device, coupling a source of a liquid to a vial input port, flowing the liquid into the vial to force the thawed biological material into the dispersion assembly and through a dispersion element and a one-way valve within a tubular barrel of the delivery device to disperse the thawed biological material into the tubular barrel, flowing the liquid through a filter assembly coupled to a dispensing end of the tubular barrel, the filter assembly including a filter medium, the filter medium sized to prevent the dispersed biological material from passing through the filter assembly but to permit the liquid to pass through the filter assembly, and forcing the dispersed biological material out of the delivery device and into an intravascular device coupled to the delivery device.

Example 15 is the method of Example 14, wherein forcing the dispersed biological material out of the delivery device and into the intravascular device coupled to the delivery device includes selecting the filter assembly to be in a bypass state so the liquid and the dispersed biological material can bypass the filter medium and moving the vial toward filter assembly to force the coupled dispersion assembly to slide along the tubular barrel and toward the dispensing end of the tubular barrel, the dispersion assembly forcing the biological material through the filter assembly and into the intravascular device coupled to the delivery device.

Example 16 is a device for aseptic delivery of biological material from a vial. The device includes a tubular barrel, a filter assembly, and a dispersion assembly. The tubular barrel includes a receiving end to accept a portion of the vial within the tubular barrel and a dispensing end opposite the receiving end. The filter assembly is fluidly connected to the dispensing end of the tubular barrel. The dispersion assembly has a proximal end configured to couple to the vial and a distal end opposite the proximal end. The dispersion assembly is configured to be at least partially disposed within the tubular barrel. The dispersion assembly includes a dispersion element, a piston, and a one-way valve. The dispersion element is configured to be in fluid communication with the vial to disperse the biological material from the vial. The dispersion element includes a wall forming a plurality of openings through the wall. The piston is disposed at the distal end of the dispersion assembly. The piston is in sealing contact with the tubular barrel. The one-way valve forms a fluid passageway in fluid communication with the dispersion element and the tubular barrel. The one-way valve is configured to allow a flow of the dispersed biological material from the dispersion element, through the fluid passageway, and into the tubular barrel, and to prevent a flow of the dispersed biological material from the tubular barrel into the dispersion assembly.

Example 17 is the device of Example 16, wherein the filter assembly includes a filter medium, the filter assembly selectable between an open state wherein the filter medium prevents the biological material from passing through the filter assembly but permits liquid to pass through the filter assembly, a bypass state wherein the biological material can pass through the filter assembly to deliver the biological material, and, optionally, a closed state wherein no liquid or biological material can pass through the filter assembly.

Example 18 is the device of Example 17, wherein the filter assembly further includes a filter medium assembly configured to support the filter medium.

Example 19 is the device of Example 18, wherein the filter medium assembly is detachable from the filter assembly.

Example 20 is the device of Example 17, wherein the filter assembly further includes a filter output port in fluid communication with the dispensing end of the tubular barrel when the filter assembly is in the open state and a bypass output port in fluid communication with the dispensing end of the tubular barrel when the filter assembly is in the bypass state.

Example 21 is the device of Example 20, wherein the filter assembly further includes a filter base and a filter selector. The filter base includes a first section in fluid communication with the filter output port, a second section in fluid communication with the bypass output port, and a third section that is not in fluid communication with either of the filter output port or the bypass output port. The filter selector is rotatably coupled to the filter base. The filter selector includes a filter inlet in fluid communication with the tubular barrel. The filter selector is configured to fluidly connect the filter inlet to the first section, the second section, or the third section of the filter base as the filter selector rotates relative to the filter base.

Example 22 is the device of Example 21, wherein the filter assembly further includes a compression clasp coupled to the filter base to force the filter selector into sealing contact with the filter base and a wrench coupled to the filter selector.

Example 23 is the device of any of Examples 16-22, wherein the plurality of openings through the wall are sized to permit the passage of dispersed biological material through the wall and to prevent the passage of undispersed biological material through the wall.

Example 24 is the device of any of Examples 16-23, wherein the tubular barrel further includes a barrel ventilation passageway extending through a wall of the tubular barrel from a first location between the dispensing end and the receiving end to a second location adjacent to the receiving end.

Example 25 is the device of Example 24, wherein the tubular barrel further includes a one-way barrel vent valve within the barrel ventilation passageway and configured to allow the passage of gases away from the first location, prevent the passage of gases toward the first location, and prevent the passage of liquids.

Example 26 is a system for aseptic storage and delivery of biological material. The system includes a vial and a device for aseptic delivery of biological material from the vial. The vial includes a tubular body to contain the biological material until delivery, a vial input port, and a vial output port including a luer activated valve. The device includes a tubular barrel, a filter assembly, and a dispersion assembly. The tubular barrel includes a receiving end to accept a portion of the vial within the tubular barrel, and a dispensing end opposite the receiving end. The filter assembly is fluidly connected to the dispensing end of the tubular barrel. The dispersion assembly has a proximal end and a distal end opposite the proximal end. The proximal end configured to open the luer activated valve when coupled to the vial output port to bring the dispersion element into fluid communication with the vial. The dispersion assembly is configured to be at least partially disposed within the tubular barrel. The dispersion assembly includes a dispersion element, a piston, and a one-way valve. The dispersion element is configured to be in fluid communication with the vial to disperse the biological material from the vial. The dispersion element includes a wall forming a plurality of openings through the wall. The piston is disposed at the distal end of the dispersion assembly. The piston is in sealing contact with the tubular barrel. The one-way valve forms a fluid passageway in fluid communication with the dispersion element and the tubular barrel. The one-way valve is configured to allow a flow of the dispersed biological material from the dispersion element, through the fluid passageway, and into the tubular barrel, and to prevent a flow of the dispersed biological material from the tubular barrel into the dispersion assembly.

Example 27 is the system of Example 26, wherein the tubular barrel further includes a barrel ventilation passageway extending through a wall of the tubular barrel from the dispensing end to the receiving end.

Example 28 is the system of either of Examples 26 or 27, wherein the vial further includes a vial ventilation passageway extending through a wall of the vial from vial output port to the vial input port.

Example 29 is the system of Example 28, wherein the vial further includes a one-way vial vent valve within the vial ventilation passageway and configured to allow the passage of gases away from the vial output port, prevent the passage of gases toward the vial output port, and prevent the passage of liquids.

Example 30 is the system of any of Examples 26-29, wherein the filter assembly includes a filter medium, the filter assembly selectable between an open state wherein the filter medium prevents the biological material from passing through the filter assembly but permits liquid to pass through the filter assembly, a bypass state wherein the biological material can pass through the filter assembly to deliver the biological material, and, optionally, a closed state wherein no liquid or biological material can pass through the filter assembly.

31. The system of Example 30, wherein the filter assembly further includes a filter medium assembly configured to support the filter medium.

32. The system of either of Examples 30 or 31, wherein the filter assembly further includes a filter base and a filter selector. The filter base including a first section, a second section, and a third section. The first section is in fluid communication with a filter output port. The filter output port is in fluid communication with the dispensing end of the tubular barrel when the filter assembly is in the open state. The second section is in fluid communication with a bypass output port. The bypass output port is in fluid communication with the dispensing end of the tubular barrel when the filter assembly is in the bypass state. The third section is not in fluid communication with either of the filter output port or the bypass output port. The filter selector is rotatably coupled to the filter base. The filter selector includes a filter inlet in fluid communication with the tubular barrel. The filter selector is configured to fluidly connect the filter inlet to the first section, the second section, or the third section of the filter base as the filter selector rotates relative to the filter base.

Example 33 is the system of Example 32, wherein the filter assembly further includes a compression clasp coupled to the filter base to force the filter selector into sealing contact with the filter base, and a wrench coupled to the filter selector.

Example 34 is a method for the aseptic delivery of biological material that is in an aseptically frozen and condensed state within a vial using a delivery device. The method includes thawing the biological material contained within the vial, coupling a vial output port of the vial to proximal end of a dispersion assembly of the delivery device, coupling a source of a liquid to a vial input port, flowing the liquid into the vial to force the thawed biological material into the dispersion assembly and through a dispersion element and a one-way valve within a tubular barrel of the delivery device to disperse the thawed biological material into the tubular barrel, flowing the liquid through a filter assembly coupled to a dispensing end of the tubular barrel, the filter assembly including a filter medium, the filter medium sized to prevent the dispersed biological material from passing through the filter assembly but to permit the liquid to pass through the filter assembly, and forcing the dispersed biological material out of the delivery device and into an intravascular device coupled to the delivery device.

Example 35 is the method of Example 34, wherein forcing the dispersed biological material out of the delivery device and into the intravascular device coupled to the delivery device includes selecting the filter assembly to be in a bypass state so the liquid and the dispersed biological material can bypass the filter medium, and moving the vial toward filter assembly to force the coupled dispersion assembly to slide along the tubular barrel and toward the dispensing end of the tubular barrel, the dispersion assembly forcing the biological material through the filter assembly and into the intravascular device coupled to the delivery device.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

The above-mentioned and other features and advantages of this disclosure, and the manner of attaining them, will become more apparent and the invention itself will be better understood by reference to the following descriptions of embodiments of the invention taken in conjunction with the accompanying drawings, wherein.

Figure 1:
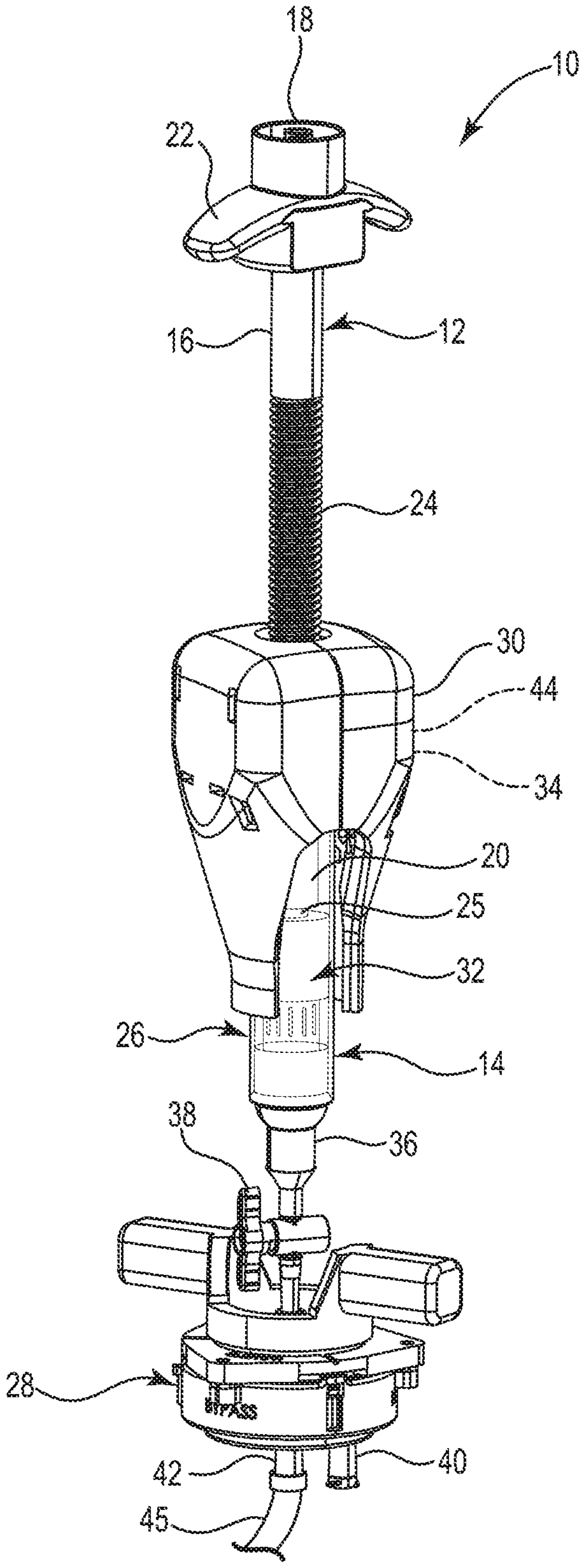
FIG. 1 is a perspective view of a system for aseptic storage and delivery of biological material, according to some embodiments of the disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Embodiments of the present disclosure include a system for the aseptic storage and delivery of biological material, such as transplant cells for cellular therapy. Embodiments can provide for a closed aseptic system beginning after the production of the transplant cells and maintains the closed aseptic system for the transplant cells through freezing, transport, storage, thawing, washing, and delivery into the patient.

FIG. 1 is a perspective view of a system 10 for aseptic storage and delivery of biological material, according to embodiments of the disclosure. As shown in FIG. 1, the system 10 includes a vial 12 and a delivery device 14. The vial 12 can include a tubular body 16, a vial input port 18, a vial output port 20, a handle 22 and a plurality of threads 24. In the embodiment of FIG. 1, the vial input port 18 and the vial output port 20 are located at opposite ends of the tubular body 16. The vial output port 20 includes a luer activated valve 25. The handle 22 can be located near the vial input port 18. The plurality of threads 24 extend along at least a portion of the tubular body 16.

The delivery device 14 includes a tubular barrel 26 (shown as transparent), a filter assembly 28, and a dispersion assembly 32. In some embodiments, the delivery device 14 may further include a vial engagement assembly 30. The tubular barrel 26 includes a receiving end 34 (not visible in within the vial engagement assembly 30, see FIG. 4) and a dispensing end 36 opposite the receiving end 34. The filter assembly 28 can include a stopcock 38, a filter output port 40 and a bypass output port 42. The vial engagement assembly 30 can include a thread disengagement pushbutton 44 (shown in FIG. 9A) for selectively disengaging the vial engagement assembly 30 from the plurality of threads 24, as described below in reference to FIGS. 9A-9C.

The filter assembly 28 is configured to fluidly connect to the dispensing end 36 of the tubular barrel 26. The vial engagement assembly 30 is connected to the receiving end 34 of the tubular barrel 26. The dispersion assembly 32 is configured to connect to the vial output port 20, as described in further detail below in reference to FIG. 4. The dispersion assembly 32 is configured to be disposed at least partially within the tubular barrel 26 and can be slideably engaged with the tubular barrel 26. So configured, the vial 12, the dispersion assembly 32, and the tubular barrel 26 can act as a syringe, with the vial 12 and the dispersion assembly 32 acting together as a plunger and the tubular barrel 26 acting as the syringe body.

In use, thawed biological material including cryoprotectant within the vial 12 can be forced out of the vial 12 by a flow of liquid (such as saline solution or a delivery matrix) connected to the vial input port 18, and into the dispersion assembly 32. The biological material, the cryoprotectant and the liquid can flow through the dispersion assembly 32, and into the tubular barrel 26 between the dispersion assembly 32 and the filter assembly 28. As the biological material, the cryoprotectant and the liquid flow through the dispersion assembly 32, the biological material is dispersed. That is, clumps of cells of the biological material are broken up into individual cells, or at least into smaller groups of cells, as described in detail below in reference to FIG. 4. The filter assembly 28 can be configured to be in an open state in which a filter medium 112 (shown in FIG. 8) prevents the dispersed biological material from passing through the filter assembly 28, but permits the cryoprotectant and the liquid to pass through the filter medium 112 and out through the filter output port 40 to permit the flow of liquid through the vial 12 and the delivery device 14. The flow of liquid may be maintained so as to disperse the biological material and wash the cryoprotectant from the biological material.

Optionally, once the biological material has been dispersed into the tubular barrel 26 and washed, another source of liquid (such as a saline solution or a delivery matrix) can be connected to the filter output port 40, and the vial 12 and dispersion assembly 32 can be pulled away from the filter assembly 28, drawing liquid across the filter medium 112 to dislodge any dispersed biological material from the filter medium 112, and to provide a desired concentration of biological material and liquid for delivery to the patient.

Once the dispersed biological material and liquid are ready for delivery to the patient, the stopcock 38 can be closed, and the filter assembly 28 can be configured to be in a bypass state in which the dispersed biological material and liquid can pass through the filter assembly 28 and out through the bypass output port 42 to the patient by way of an intravascular device 45 attached to the bypass output port 42. Such intravascular devices 45 can include, for example, intravenous lines or needles. Once the filter assembly 28 is configured to be in the bypass state and the intravascular device 45 is attached to the bypass output port 42, the stopcock 38 can be opened, and the vial 12 moved toward the dispensing end 36 of the tubular barrel 26 to force the dispersion assembly 32 toward the filter assembly 28 to deliver the biological material and liquid to the patient.

In the embodiment shown in FIG. 1, the vial 12 can be moved relative to the delivery device 14 in a precise fashion by rotating the vial 12 to screw the vial 12 into or out of the delivery device 14 as the plurality of threads 24 threadily engage the vial engagement assembly 30. The handle 22 may be grasped to ease rotation of the vial 12. Should less precise and/or faster control of the movement of vial 12 relative to the delivery device 14 be desired, the thread disengagement pushbutton 44 can be pressed (as shown in FIG. 1) to disengage the vial engagement assembly 30 from the plurality of threads 24, permitting the vial 12 to be moved relative to the delivery device 14 by pushing or pulling on the vial 12, as one would with a syringe, without requiring rotation of the vial 12.

Figure 2:
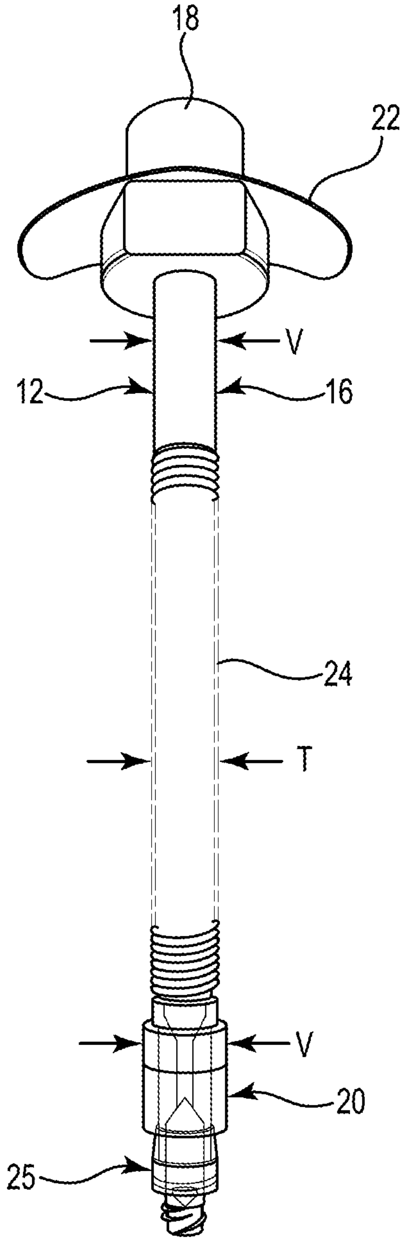
FIG. 2 is a perspective view of a vial of FIG. 1, according to some embodiments of the disclosure.

FIG. 2 is a perspective view of the vial 12 of FIG. 1, according to some embodiments of the disclosure. FIG. 2 shows more clearly the vial output port 20 including the luer activated valve 25. In the embodiment of FIG. 2, the luer activated valve 25 includes a male luer inlet and a female luer outlet. The male luer inlet includes threads configured to engage a corresponding female luer outlet on the vial 12, shown more clearly in FIG. 3. The luer activated valve 25 may be, for example, a luer activated valve #80114 available from Qosina, Ronkonkoma, NY The luer activated valve 25 is configured to prevent the flow of the biological material, cryoprotectant, and the liquid through the vial output port 20 until the luer activated valve 25 is activated by the stem of a male luer lock connection of the dispersion assembly 32, as described below in reference to FIG. 4. In some embodiments, the luer activated valve 25 may be integrally formed with the rest of the vial 12.

In some embodiments, the vial input port 18 may also include a pressure activated check valve (not shown), such as a pressure activated check valve #80107 available from Qosina, Ronkonkoma, NY, for example. The pressure activated check valve is configured to prevent the passage of the liquid through the vial input port 18 until the pressure activated check valve is connected to a line providing the liquid (not shown) at a differential pressure exceeding the cracking pressure for the pressure activated check valve. In some embodiments, the luer activated valve at the vial input port 18 may be integrally formed with the rest of the vial 12. In this way, the contents of the vial 12 is protected from contaminants and remains intact until use.

In some embodiments, the plurality of threads 24 have a thread diameter T and a portion of the vial 12 including the vial output port 20 and/or a portion of the vial 12 not including the plurality of threads 24 has a diameter V that is greater than the thread diameter T.

Figure 3:
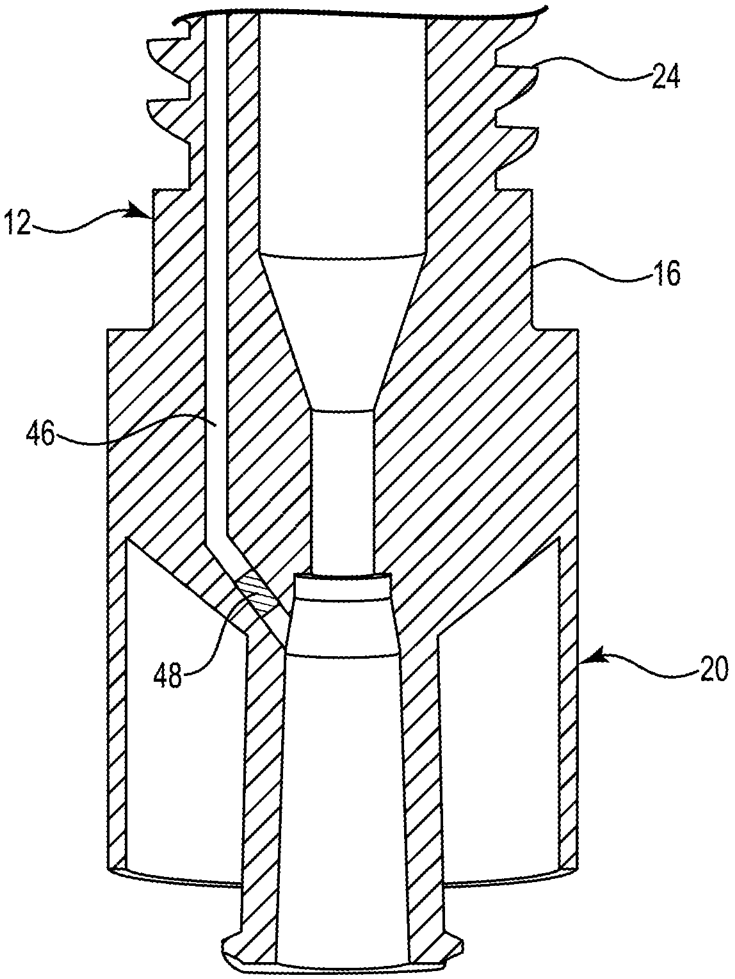
FIG. 3 is an enlarged schematic cross-sectional view of a portion of the vial of FIG. 2, according to some embodiments of the disclosure.

FIG. 3 is an enlarged schematic cross-sectional view of the vial output port 20 shown without the luer activated valve 25 for clarity to show the female luer outlet described above in reference to FIG. 2. As shown in FIG. 3, the vial 12 may further include a vial ventilation passageway 46 that extends from the vial output port 20 and terminates near the vial input port 18 (FIG. 2). The vial ventilation passageway 46 is configured to assist in evacuation of air while the biological material, the cryoprotectant, and the liquid are being forced out of the vial 12. In some embodiments, the vial 12 further comprises a one-way valve 48 disposed within the vial ventilation passageway 46. The one-way valve 48 is configured to allow the passage of gases from the vial output port 20, prevent the passage of gases to the vial output port 20, and prevent the passage of liquids. The one-way valve 48 may be a duckbill valve, such as a DU 020.001 DS available from Minivalve International, The Netherlands, or a check valve, such as a Tadpole Miniature Check Valve from Cambridge Reactor Designs, Cambridge, UK, for example.

The vial 12 is a tubular container that can be formed of any material that remains structurally sound after lengthy exposure to cryogenic temperatures and is suitable for use with biological materials. That is, the material does not present a source of contamination to the biological, for example, from materials leaching out of the material. Suitable materials can include polymer materials, such as polypropylene, polyamide, or polyimide. In some embodiments, the vial input port 18 and the vial output port 20 each further include one or more additional sterile seals (not shown). The biological material can be loaded into the vial 12 and then the additional sterile seals can be applied.

In some embodiments, after the biological material is washed and suspended in a solution including proteins and a cryoprotectant, such as dimethyl sulfoxide (DMSO), the biological material can be centrifuged and the supernatant aspirated off to produce a condensed clump of cells in a "pellet" form. The biological material in the vial 12 can be frozen in this condensed form to provide for a large number of cells in a relatively compact storage form factor. Thus, the vial 12 can be much smaller than the bag typically employed for the transportation and storage of biological material, as discussed above. The smaller form factor of the vial 12 is easier to transport and requires less freezer space, which can reduce costs. The vial 12 can be a compact and efficient device for the transportation and storage of the biological material.

Figure 4:
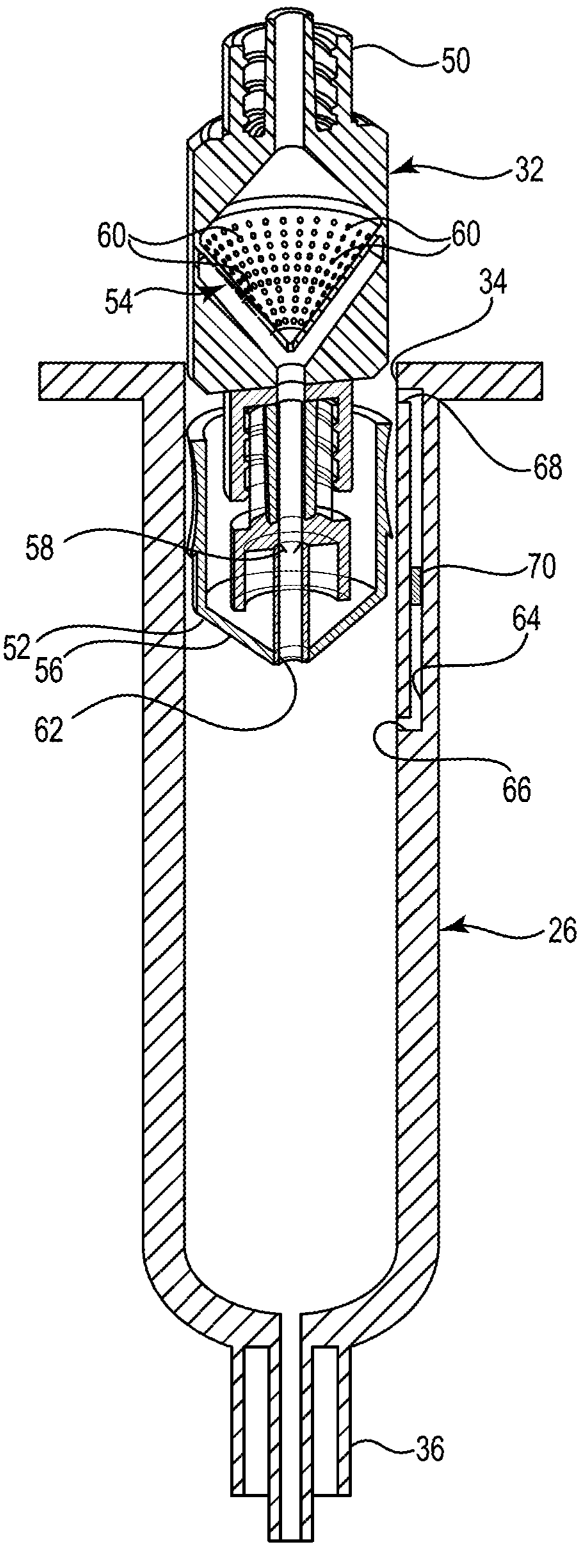
FIG. 4 is a cross-sectional view of the dispersion assembly and the tubular barrel of FIG. 1, according to some embodiments of the disclosure.

FIG. 4 is a cross-sectional view of the dispersion assembly 32 and the tubular barrel 26 of FIG. 1, according to some embodiments of the disclosure. As shown in FIG. 4, the dispersion assembly 32 is configured to be at least partially disposed within the tubular barrel 26. The dispersion assembly 32 has a proximal end 50 and a distal end 52 opposite the proximal end 50. The dispersion assembly 32 includes a dispersion element 54, a piston 56, and a one-way valve 58.

The dispersion element 54 includes a plurality of holes 60 through the dispersion element 54. In some embodiments, each of the holes 60 may be sized such that they will disperse cells of the biological material by permitting the passage of individual cells, but not permit the passage of clumps of cells. In some other embodiments, each of the holes 60 may be sized such that they will disperse cells of the biological material by permitting the passage of individual cells and small clumps of cells, but not permit the passage of large clumps of cells. In some embodiments, the holes 60 can have diameters as small as 0.1 millimeters (mm). Although the plurality of holes 60 are shown as circular holes, it is understood that embodiments includes holes 60 having other shapes, such as, triangular, oval, or rectangular, for example.

In the embodiment shown in FIG. 4, the dispersion element 54 is funnel shaped to provide a large surface area for the plurality of holes 60. However, it is understood that embodiments include dispersion elements 54 having other shapes including an inverse funnel, a hemisphere, or an inverse hemisphere, for example. In some embodiments, the dispersion element 54 may be have a flat shape.

The dispersion element 54 may be made from a durable, biocompatible material, such as titanium, or polymer materials, such as polypropylene, polyamide, or polyimide. In some embodiments, the dispersion element 54 is formed by additive manufacturing from powdered titanium metal.

The piston 56 is formed of an elastomeric material, such as high-density polyethylene, for example. The piston 56 may be an Optimum® SmoothFlow™ piston available from Nordson Corporation, Westlake, OH, for example.

The one-way valve 58 may be a pressure activated check valve, such as a pressure activated check valve #80107 available from Qosina, Ronkonkoma, NY, for example. The one-way valve 58 is configured to prevent the passage of the biological material, cryoprotectant, and liquid from the dispersion element 54 until a differential pressure exceeding the cracking pressure for the pressure activated check valve is applied. The one-way valve 58 is also configured to prevent a flow of the biological material, cryoprotectant, and liquid back into the dispersion assembly 32 from the tubular barrel 26. In some embodiments, the one-way valve 58 may be integrally formed with the dispersion element 54.

The proximal end 50 of the dispersion assembly 32 is configured to couple to the luer activated valve 25. For example, in the embodiment shown in FIG. 4, the proximal end 50 is in the form of a male luer connecter configured to connect to the corresponding female luer connector of the luer activated valve 25, as described above in reference to FIG. 2. Such connectors are well known in the art.

The piston 56 is disposed at the distal end 52 of the dispersion assembly 32 and is in sealing contact with the tubular barrel 26. In the embodiment shown in FIG. 4, the one-way valve 58 couples the piston 56 to the dispersion element 54, forming a fluid passageway 62 through the piston 56. The fluid passageway 62 is in fluid communication with the dispersion element 54 and the tubular barrel 26. The one-way valve 58 is configured to allow the flow of the dispersed biological material, the cryoprotectant, and the liquid flow from the dispersion element 54, through the fluid passageway 62, and into the tubular barrel 26, as described above in reference to FIG. 1, and to prevent a back flow of dispersed biological material from the tubular barrel 26 and into the dispersion assembly 32. So configured, the dispersed biological material, the cryoprotectant, and the liquid flow may pass into the tubular barrel 26 through the one-way valve 58, and then the vial 12 and dispersion assembly 32 can acting together as a plunger with the tubular barrel 26 acting as the syringe body to dispense the dispersed biological material.

When dispersing and dispensing the biological material, air may become trapped within the tubular barrel 26. The presence of the trapped air can create difficulty in accurately dispensing the biological material due to the compressibility of the trapped air. In some embodiments, the flexibility of the piston 56 is such that as the dispersion assembly 32 is moved further into the tubular barrel 26, any trapped air will flow, or "burp", past the edge of the piston 56 where it meets the tubular barrel 26, thus eliminating the trapped air. Additionally, or alternatively, in some embodiments, the tubular barrel 26 further comprises a barrel ventilation passageway 64 that extends through a wall of the tubular barrel 26 from a first location 66 to a second location 68. The first location 66 may be between the dispensing end 36 and the receiving end 34. The second location 68 may be adjacent to the receiving end 34. The barrel ventilation passageway 64 is configured to assist in evacuation of air while the biological material, the cryoprotectant, and the liquid are being forced out of the tubular barrel 26. In some embodiments, the tubular barrel 26 further comprises a one-way valve 70 disposed within the barrel ventilation passageway 64. The one-way valve 70 is configured to allow the passage of gases from the first location 66, prevent the passage of gases to the first location 66, and prevent the passage of liquids. The one-way valve 70 may be a duckbill valve, such as a DU 020.001 DS available from Minivalve International, The Netherlands, or a check valve, such as a Tadpole Miniature Check Valve from Cambridge Reactor Designs, Cambridge, UK, for example. In some other embodiments, the one-way valve 70 may be disposed outside of the tubular barrel 26 and be coupled to the barrel ventilation passageway 64, rather than be disposed within the barrel ventilation passageway 64. Although the second location 68 is shown as venting within the tubular barrel 26, it is understood that embodiments include second locations 68 that vent outside of the tubular barrel 26.

Figure 5:
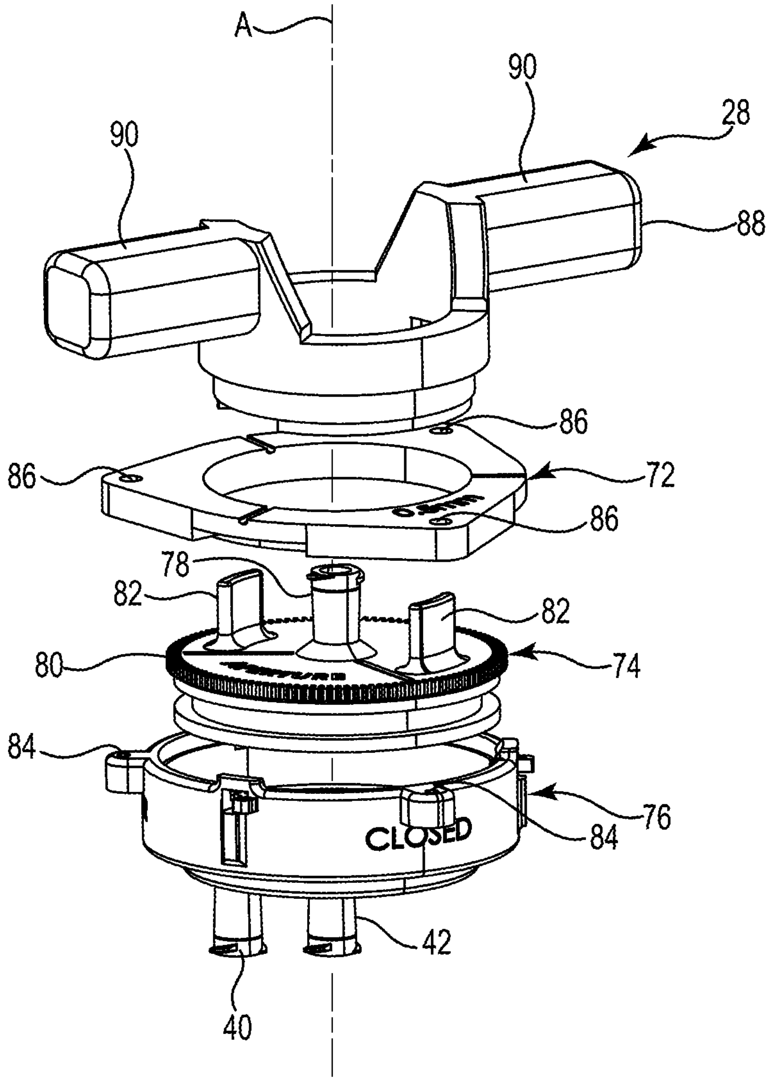
FIG. 5 is an exploded perspective view of the filter assembly of FIG. 1, according to some embodiments of the disclosure.

FIG. 5 is an exploded perspective view of the filter assembly 28 of FIG. 1, according to some embodiments of the disclosure. As shown in FIG. 5, the filter assembly 28 further includes a compression clasp 72, a filter selector 74, and a filter base 76. The filter selector 74 includes a filter inlet 78 and may further include a plurality of teeth 80 around its circumference and at least two bosses 82 projecting from a surface of the filter selector 74 opposite the filter base 76. The filter base 76 may further include a plurality of holes 84 (two of three visible in FIG. 5), in addition to the filter output port 40 and the bypass output port 42 as described above in reference to FIG. 1. The compression clasp 72 may include a plurality of holes 86, corresponding to the plurality of holes 84 in the filter base 76. In some embodiments, the filter assembly 28 may further include a wrench 88. The wrench 88 is configured to engage the at least two bosses 82 and includes at least two shoulder portions 90.

The filter inlet 78 is coupled to the stopcock 38 (FIG. 1). The filter selector 74 fits into the filter base 76 with the plurality of teeth 80 engaging a pawl (not shown) projecting radially inward from the filter base 76. The compression clasp 72 covers an outer diameter of the filter selector 74 and is coupled to the filter base 76 to hold the filter selector 74 within the filter base 76. The compression clasp 72 may be coupled to the filter base 76 by a plurality of connectors (not shown) extending between the plurality of holes 86 in the compression clasp 72 and the corresponding plurality of holes 84 in the filter base 76. The connectors may include screws, bolts, pins, or other connectors known in the art. So configured, the filter selector 74 may be rotated axially relative to the filter base 76 by the at least two bosses 82. In some embodiments, the wrench 88 may engage the at least two bosses 82 with the at least two shoulder portions 90 providing more leverage when rotating the filter selector 74 relative to the filter base 76 when compared to using the bosses 82 alone.

Figure 6:
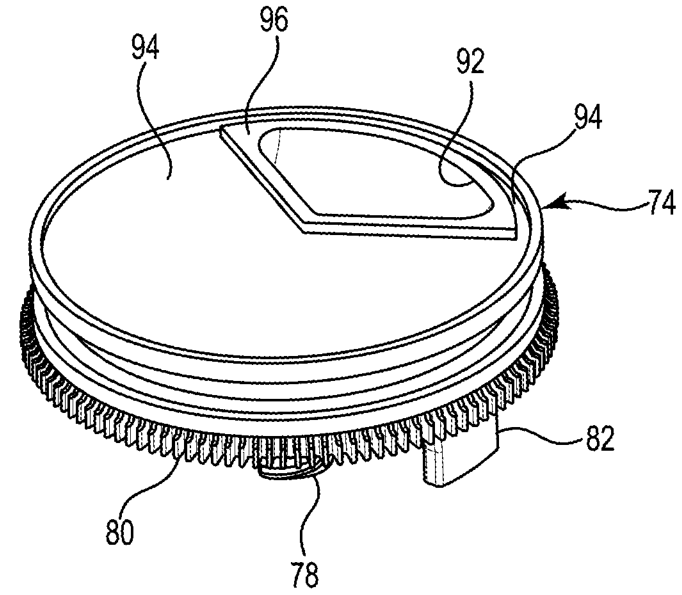
FIG. 6 is a perspective view of a filter selector of the filter assembly of FIG. 5, according to some embodiments.
Figure 7:
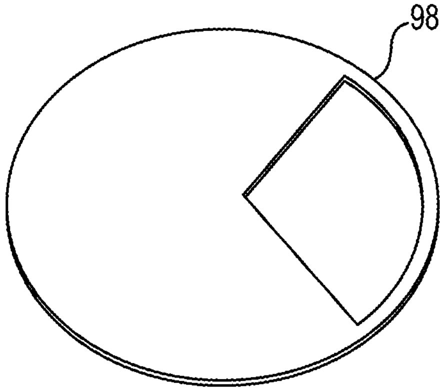
FIG. 7 is a top view of a gasket for use with the filter selector shown in FIG. 6.

FIG. 6 is a perspective view of the filter selector 74 shown in FIG. 5, according to some embodiments. As shown in FIG. 6, the filter selector 74 further includes opening 92 and recessed portion 94. The opening 92 is fluidly connected to the filter inlet 78. The recessed portion 94 surrounds the opening 92 and is separated from the opening 92 by a raised portion 96. FIG. 7 is a top view of a gasket 98 for use with the filter selector 74 shown in FIG. 6. As shown in FIG. 7, the gasket 98 is shaped to fit into the recessed portion 94 and surround the opening 92. The gasket 98 may be made from an elastomeric polymer, such as silicone, for example. The gasket 98 is thick enough to extend beyond the raised portion 96 to provide a fluid seal around the opening 92 between the between the filter selector 74 and the filter base 76.

Figure 8:
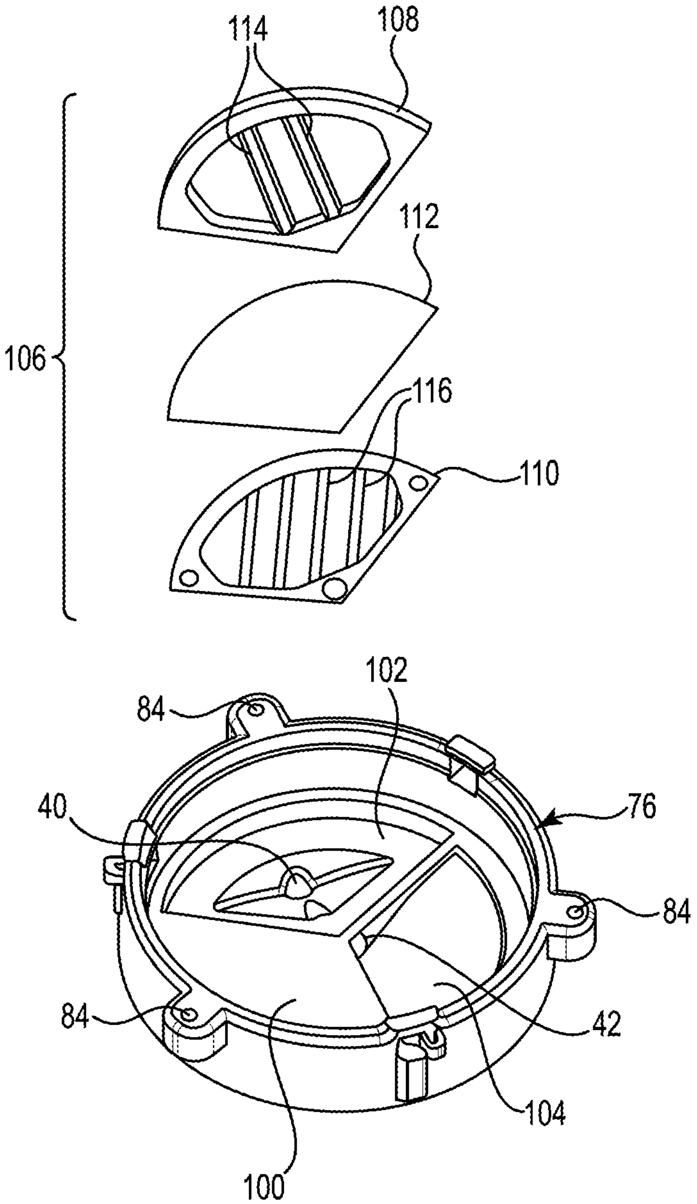
FIG. 8 is an exploded perspective view of a portion of the filter assembly shown in FIG. 5, according to some embodiments of the disclosure.

FIG. 8 is an exploded perspective view of a portion of the filter assembly 28 shown in FIG. 5, according to some embodiments of the disclosure. As shown in FIG. 8, the filter base 76 further includes three filter sections: a closed filter section 100, an open filter section 102, and a bypass filter section 104. The closed filter section 100 is an impermeable barrier that does not permit liquid or biological material to pass. In some embodiments, the closed filter section 100 is optional. The bypass filter section 104 can be a largely open section to permit the efficient passage of liquids and biological material when dispensing the biological material through the bypass output port 42 and into the intravascular device 45 (FIG. 1). The open filter section 102 includes a filter medium assembly 106. The filter medium assembly 106 includes an upper clamp 108, a lower clamp 110, and a filter medium 112. The upper clamp 108 includes at least one upper support bar 114 and the lower clamp 110 includes at least one lower support bar 116.

The filter medium 112 is a porous medium including pores that are large enough to permit the efficient passage of the cryoprotectant and the liquid through the filter output port 40, but small enough to substantially prevent the passage of the cells of the biological material through the filter output port 40. In some embodiments, the pore size may be as small as 0.22 microns or 0.45 microns, for example. The filter medium 112 may be made of a material suitable for use with biological materials. That is, the material does not present a source of contamination to the biological materials, for example, from materials leaching out of the material. Suitable materials include polymer materials, such as polytetrafluoroethylene (PTFE), for example.

The upper clamp 108 couples to the lower clamp 110 to contain the filter medium 112 between the upper clamp 108 and the lower clamp 110. The filter medium 112 is supported by the lower support bars 116 when fluid flows out of the filter output port 40 and by the upper support bars 114 when fluid flows back into the filter assembly 28 thorough the filter output port 40. In some embodiments, the filter medium assembly 106 may be detachable from the filter assembly 28 for cleaning or replacement of the filter medium assembly 106.

Considering FIGS. 5-8 together, the filter selector 74 is rotatable relative to the filter base 76 about an axis A such that any of the three filter sections: the closed filter section 100, the open filter section 102, and the bypass filter section 104 can be selected to be in fluid contact with dispensing end 36 of the tubular barrel 26 through the opening 92, the filter inlet 78, and the stopcock 38. The opening 92 and surrounding gasket 98 are sized such that liquid and biological material flowing out of the opening 92 and into one of the three filter sections 100,102, and 104, are prevented from leaking into either of the other of the three filter sections 100,102, and 104, or from between the filter selector 74 and the filter base 76.

Thus, the filter assembly 28 is selectable between an open state in which the filter medium 112 prevents the biological material from passing through the filter assembly 28 but permits liquid to pass through the filter assembly 28, a bypass state wherein the biological material can pass through the filter assembly 28 to deliver the biological material, and a closed state wherein no liquid or biological material can pass through the filter assembly 28. The open state may be employed during washing of the biological material and dispersal of the cells into the tubular barrel 26. The bypass state may be employed during delivery of the biological material to the patient. The closed state may be employed prior to use of the delivery device 14 to protect the filter medium 112.

The pawl (not shown) can be angled such that it engages the plurality of teeth 80 to form a one-way ratchet to permit the filter selector 74 to rotate in one direction only, relative to the filter base 76. Thus, in this embodiment, the filter assembly 28 is only selectable from the closed state to the open state and from the open state to the bypass state. This arrangement prevents the filter selector 74 from accidentally moving from the closed state directly to the bypass state, which could result in the loss of the biological material. Additionally, or alternatively, the exteriors of the filter selector 74 and the filter base 76 can be marked to provide a visual indicator the state of the filter assembly 28.

In other embodiments, the filter assembly 28 does not include the closed state. In such embodiments, the filter selector 74 may not include the plurality of teeth 80, and the filter base 76 may not include the closed filter section 100 or the pawl.

Figure 9A:
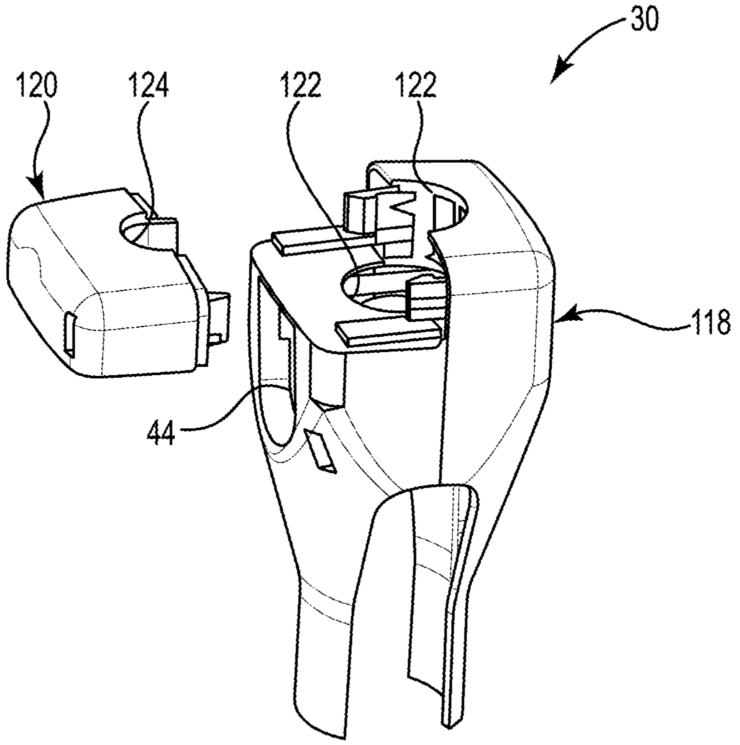
FIGS. 9A-9C are views of a vial engagement assembly of the delivery device of FIG. 1, according to some embodiments of the disclosure.
Figure 9B:
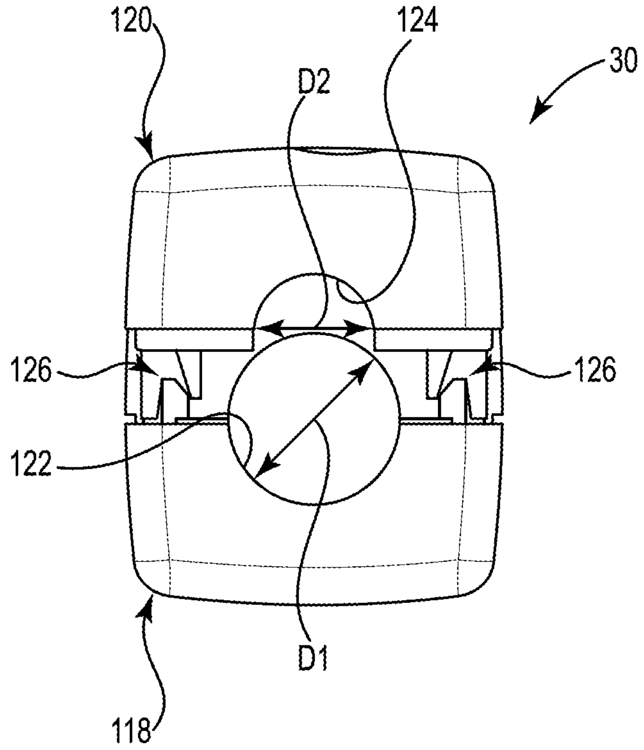
Figure 9C:
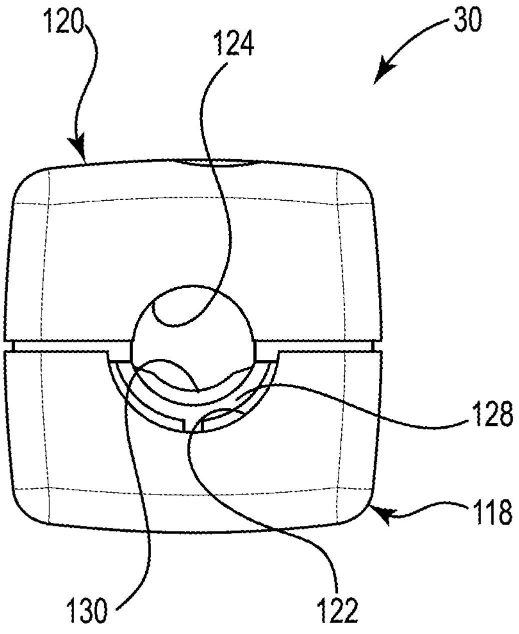

FIGS. 9A-9C are views of the vial engagement assembly 30 of the delivery device 14 of FIG. 1, according to some embodiments. As discussed above in reference to FIG. 2, in some embodiments, the plurality of threads 24 of the vial 12 have the thread diameter T and the portion of the vial 12 including the vial output port 20 and has a diameter V that is greater than the thread diameter T. The vial engagement assembly 30 is configured to accommodate both diameters T and V of the vial 12. FIG. 9A is an exploded perspective view of the vial engagement assembly 30 showing that the vial engagement assembly 30 includes a main housing 118 and a support housing 120. The main housing 118 includes a first opening 122 through the main housing 118. The support housing 120 includes a second opening 124. The support housing 120 is configured to be selectively connected to the main housing 118.

FIG. 9B is an exploded top view of the vial engagement assembly 30 just as the support housing 120 is being connected to the main housing 118 by two snap joints 126. As shown in FIG. 9B, the first opening 122 has diameter D1 and the second opening 124 has a diameter D2. The diameter D1 is slightly greater than the diameter V of the vial 12 to accommodate passage of the portion of the vial 12 including the vial output port 20. The diameter D2 is slightly larger than the diameter T, but smaller than either the diameter D1 or the diameter V to provide support for the portion of the vial 12 including the plurality of threads 24 as the vial 12 passes through the vial engagement assembly 30.

FIG. 9C is a top view of the vial engagement assembly 30 once the support housing 120 is fully engaged with the main housing 118 and held in a fixed position by the snap joints 126. As shown in FIG. 9C, the vial engagement assembly 30 further includes a moveable thread 128. The moveable thread 128 includes a thread portion 130. The moveable thread 128 is connected to the thread disengagement pushbutton 44 so that when the thread disengagement pushbutton 44 is pushed in, as shown in FIGS. 9A and 9B, the moveable thread 128 is pushed outside of the radius D1 of the first opening 122. When the thread disengagement pushbutton 44 is released, springs (not shown) inside the main housing 118 force the moveable thread 128 inside of the radius D1 of the first opening 122, as shown in FIG. 9C. When the moveable thread 128 is forced inside the radius D1, the thread portion 130 is forced inside the radius D2 where it can threadily engage the plurality of threads 24 of the vial 12. In this way, the vial engagement assembly 30 is configured to selectively engage the plurality of threads 24.

The vial 12 can be moved in a precise fashion by rotation the vial 12 to screw the vial 12 into or out of the delivery device 14 as the plurality of threads 24 threadily engage the vial engagement assembly 30. Alternatively, the thread disengagement pushbutton 44 can be pressed to disengage the vial engagement assembly 30 from the plurality of threads 24 as described above, permitting the vial 12 and coupled dispersion assembly 32 (FIG. 1) to be moved through the tubular barrel 26 by pushing or pulling on the vial 12, as one would with a syringe, without requiring rotation of the vial 12.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A device for aseptic delivery of biological material from a vial, the device comprising:
- a tubular barrel comprising:
  - a receiving end to accept a portion of the vial within the tubular barrel; and
  - a dispensing end opposite the receiving end;
- a filter assembly fluidly connected to the dispensing end of the tubular barrel; and
- a dispersion assembly having a proximal end configured to couple to the vial and a distal end opposite the proximal end, the dispersion assembly configured to be at least partially disposed within the tubular barrel, the dispersion assembly comprising:
  - a dispersion element configured to be in fluid communication with the vial to disperse the biological material from the vial, the dispersion element comprising a wall forming a plurality of openings through the wall;
  - a piston disposed at the distal end of the dispersion assembly, the piston in sealing contact with the tubular barrel; and
  - a one-way valve forming a fluid passageway in fluid communication with the dispersion element and the tubular barrel, the one-way valve configured to allow a flow of the dispersed biological material from the dispersion element, through the fluid passageway, and into the tubular barrel, and to prevent a flow of the dispersed biological material from the tubular barrel into the dispersion assembly;
- wherein the filter assembly includes a filter medium, the filter assembly selectable between an open state wherein the filter medium prevents the biological material from passing through the filter assembly but permits liquid to pass through the filter assembly, a bypass state wherein the biological material can pass through the filter assembly to deliver the biological material, and, optionally, a closed state wherein no liquid or biological material can pass through the filter assembly.

2. The device of claim 1, wherein the plurality of openings through the wall are sized to permit the passage of dispersed biological material through the wall and to prevent the passage of undispersed biological material through the wall.

3. The device of claim 1, wherein the filter assembly further includes a filter medium assembly configured to support the filter medium.

4. The device of claim 3, wherein the filter medium assembly is detachable from the filter assembly.

5. The device of claim 1, wherein the filter assembly further includes:
- a filter output port in fluid communication with the dispensing end of the tubular barrel when the filter assembly is in the open state; and
- a bypass output port in fluid communication with the dispensing end of the tubular barrel when the filter assembly is in the bypass state.

6. The device of claim 5, wherein the filter assembly further comprises:
- a filter base comprising:
  - a first section in fluid communication with the filter output port;
  - a second section in fluid communication with the bypass output port; and
  - a third section that is not in fluid communication with either of the filter output port or the bypass output port; and
- a filter selector rotatably coupled to the filter base, the filter selector comprising a filter inlet in fluid communication with the tubular barrel, the filter selector configured to fluidly connect the filter inlet to the first section, the second section, or the third section of the filter base as the filter selector rotates relative to the filter base.

7. The device of claim 6, wherein the filter assembly further comprises:
- a compression clasp coupled to the filter base to force the filter selector into sealing contact with the filter base; and
- a wrench coupled to the filter selector.

8. The device of claim 1, wherein the tubular barrel further comprises a barrel ventilation passageway extending through a wall of the tubular barrel from a first location between the dispensing end and the receiving end to a second location adjacent to the receiving end.

9. The device of claim 8, wherein the tubular barrel further comprises a one-way barrel vent valve within the barrel ventilation passageway and configured to allow the passage of gases away from the first location, prevent the passage of gases toward the first location, and prevent the passage of liquids.

10. A system for aseptic storage and delivery of biological material, the system comprising:
- a vial comprising:
  - a tubular body to contain the biological material until delivery;
  - a vial input port; and
  - a vial output port comprising a luer activated valve; and
- a device for aseptic delivery of biological material from the vial, the device comprising:
  - a tubular barrel comprising:
    - a receiving end to accept a portion of the vial within the tubular barrel; and
    - a dispensing end opposite the receiving end;
  - a filter assembly fluidly connected to the dispensing end of the tubular barrel; and
  - a dispersion assembly having a proximal end and a distal end opposite the proximal end, the proximal end configured to open the luer activated valve when coupled to the vial output port to bring a dispersion element into fluid communication with the vial, the dispersion assembly configured to be at least partially disposed within the tubular barrel, the dispersion assembly comprising:
    - the dispersion element configured to be in fluid communication with the vial to disperse the biological material from the vial, the dispersion element comprising a wall forming a plurality of openings through the wall;
    - a piston disposed at the distal end of the dispersion assembly, the piston in sealing contact with the tubular barrel; and
    - a one-way valve forming a fluid passageway in fluid communication with the dispersion element and the tubular barrel, the one-way valve configured to allow a flow of the dispersed biological material from the dispersion element, through the fluid passageway, and into the tubular barrel, and to prevent a flow of the dispersed biological material from the tubular barrel into the dispersion assembly.

11. The system of claim 10, wherein the tubular barrel further comprises a barrel ventilation passageway extending through a wall of the tubular barrel from the dispensing end to the receiving end.

12. The system of claim 10, wherein the vial further comprises a vial ventilation passageway extending through a wall of the vial from vial output port to the vial input port.

13. The system of claim 12, wherein the vial further comprises a one-way vial vent valve within the vial ventilation passageway and configured to allow the passage of gases away from the vial output port, prevent the passage of gases toward the vial output port, and prevent the passage of liquids.

14. The system of claim 10, wherein the filter assembly includes a filter medium, the filter assembly selectable between an open state wherein the filter medium prevents the biological material from passing through the filter assembly but permits liquid to pass through the filter assembly, a bypass state wherein the biological material can pass through the filter assembly to deliver the biological material, and, optionally, a closed state wherein no liquid or biological material can pass through the filter assembly.

15. The system of claim 14, wherein the filter assembly further includes a filter medium assembly configured to support the filter medium.

16. The system of claim 14, wherein the filter assembly further comprises:

a filter base comprising:

a first section in fluid communication with a filter output port, the filter output port in fluid communication with the dispensing end of the tubular barrel when the filter assembly is in the open state;

a second section in fluid communication with a bypass output port, the bypass output port in fluid communication with the dispensing end of the tubular barrel when the filter assembly is in the bypass state; and a third section that is not in fluid communication with either of the filter output port or the bypass output port; and a filter selector rotatably coupled to the filter base, the filter selector comprising a filter inlet in fluid communication with the tubular barrel, the filter selector configured to fluidly connect the filter inlet to the first section, the second section, or the third section of the filter base as the filter selector rotates relative to the filter base.

17. The system of claim 16, wherein the filter assembly further comprises:

a compression clasp coupled to the filter base to force the filter selector into sealing contact with the filter base; and a wrench coupled to the filter selector.

18. A device for aseptic delivery of biological material from a vial, the device comprising:

a tubular barrel comprising:

a receiving end to accept a portion of the vial within the tubular barrel;

a dispensing end opposite the receiving end; and a barrel ventilation passageway extending through a wall of the tubular barrel from a first location between the dispensing end and the receiving end to a second location adjacent to the receiving end;

a filter assembly fluidly connected to the dispensing end of the tubular barrel; and a dispersion assembly having a proximal end configured to couple to the vial and a distal end opposite the proximal end, the dispersion assembly configured to be at least partially disposed within the tubular barrel, the dispersion assembly comprising:

a dispersion element configured to be in fluid communication with the vial to disperse the biological material from the vial, the dispersion element comprising a wall forming a plurality of openings through the wall;

a piston disposed at the distal end of the dispersion assembly, the piston in sealing contact with the tubular barrel; and a one-way valve forming a fluid passageway in fluid communication with the dispersion element and the tubular barrel, the one-way valve configured to allow a flow of the dispersed biological material from the dispersion element, through the fluid passageway, and into the tubular barrel, and to prevent a flow of the dispersed biological material from the tubular barrel into the dispersion assembly.

19. The device of claim 18, wherein the tubular barrel further comprises a one-way barrel vent valve within the barrel ventilation passageway and configured to allow the passage of gases away from the first location, prevent the passage of gases toward the first location, and prevent the passage of liquids.

* * * * *